United States Patent [19]

Marumo et al.

[11] Patent Number: 4,933,314
[45] Date of Patent: Jun. 12, 1990

[54] MOLECULAR SIEVING CARBON

[75] Inventors: Chisato Marumo, Neyagawa; Eiji Hayata; Niro Shiomi, both of Osaka, all of Japan

[73] Assignee: Kanebo Ltd., Tokyo, Japan

[21] Appl. No.: 165,525

[22] Filed: Mar. 8, 1988

[30] Foreign Application Priority Data

Mar. 10, 1987 [JP] Japan .................................. 62-55012

[51] Int. Cl.$^5$ ...................... C01B 31/10; C01B 53/04; B01J 20/20
[52] U.S. Cl. ........................................ 502/416; 55/26; 55/58; 55/62; 55/68; 55/75; 423/445; 423/449; 502/430; 502/432; 502/437
[58] Field of Search ............... 502/180, 416, 417, 418, 502/420, 430, 432, 437; 423/445, 449

[56] References Cited

U.S. PATENT DOCUMENTS

| Re. 32,319 | 12/1986 | Korb et al. ........................ 423/449 |
| 3,454,502 | 7/1969 | Hiltgen et al. ................... 502/527 X |
| 3,545,622 | 12/1970 | Sakhnovsky et al. ............. 55/389 X |
| 3,573,122 | 3/1971 | Olstowski et al. ............. 264/29.1 X |
| 3,639,266 | 2/1972 | Battista ................................ 502/432 |
| 3,801,513 | 4/1974 | Munzner et al. ....................... 55/75 |
| 4,024,226 | 5/1977 | Lersmacher et al. ......... 264/29.1 X |
| 4,029,600 | 6/1977 | Schmitt, Jr. et al. ............... 252/444 |
| 4,082,694 | 4/1978 | Wennerberg et al. ............. 502/427 |
| 4,154,704 | 5/1979 | Vinton et al. .................. 502/432 X |
| 4,205,055 | 5/1980 | Maire et al. ..................... 264/29.1 X |
| 4,234,326 | 11/1980 | Bailey et al. ..................... 55/387 X |
| 4,350,672 | 9/1982 | Layden, Jr. et al. .......... 264/29.1 X |
| 4,381,929 | 5/1983 | Mizuno et al. ......................... 55/387 |
| 4,399,052 | 8/1983 | Sugino .......................... 264/29.1 X |
| 4,439,349 | 3/1984 | Everett et al. ...................... 502/180 |
| 4,444,572 | 4/1984 | Avon et al. ............................. 55/26 |
| 4,526,887 | 7/1985 | Sutt, Jr. .............................. 502/420 |
| 4,629,476 | 12/1986 | Sutt, Jr. ................................. 55/74 |
| 4,790,859 | 12/1988 | Marumo et al. ........................ 55/68 |

FOREIGN PATENT DOCUMENTS

| 0198171 | 2/1986 | European Pat. Off. . |
| 0264523 | 4/1988 | European Pat. Off. ............ 502/416 |
| 1299289 | 7/1969 | Fed. Rep. of Germany . |
| 3214771 | 10/1983 | Fed. Rep. of Germany .......... 55/25 |
| 75690 | 6/1977 | Japan ..................................... 55/389 |
| 120509 | 7/1983 | Japan ..................................... 423/445 |
| 7804596 | 10/1979 | Netherlands ........................... 55/26 |

Primary Examiner—Paul E. Konopka
Attorney, Agent, or Firm—Flynn, Thiel, Boutell & Tanis

[57] ABSTRACT

A molecular sieving carbon characterized by (A) having a structure in which a number of spherical carbonaceous particles having a particle diameter of 0.8 to 120 micrometers overlap and coalesce three-dimensionally at random, (B) in which continuous pathways running three-dimensionally at random exist between a number of the carbonaceous particles, (C) in which a number of the carbonaceous particles have each a number of micropores communicating with the pathways existing between the particles, and (D) having a carbon content of at least 85% by weight. The molecular sieving carbon is useful for obtaining, for example, a nitrogen gas, oxygen gas or gaseous mixture enriched with either the nitrogen gas or the oxygen gas from a gaseous mixture containing the nitrogen gas and oxygen gas.

12 Claims, 2 Drawing Sheets

MOLECULAR SIEVING CARBON

The present invention relates to a molecular sieving carbon, process for its production and its use. More particularly, it relates to a molecular sieving carbon which is applied in the field of separating and purifying mixed gases by the molecular sieving effect of fine pores or the like, a process for its production and its use.

Heretofore, as adsorbents producing the molecular sieving effect, silica-alumina type zeolites have widely been used and have played an important role in the separation and purification of gases. The said zeolite type molecular sieves, however, are polar and hydrophilic and inferior in thermal stability and chemical resistance, and entail the defect that they are strong in selective adsorbability for such polar substances as water that they do not show the molecular sieving effect in the presence of polar substances.

Incidentally, recently, it has become possible to prepare molecular sieves using, as material, non-polar and hydrophobic carbons. The molecular sieving carbons of this kind are excellent in thermal stability and chemical resistance, and attract attention as molecular sieves usable even in the presence of polar substances.

Japanese Patent Publication No. 37,036/1974 discloses a process of adsorbing on activated carbon a raw material substance to make phenol type resins or furan type resins by polymerization or condensation, causing its polymerization or condensation and then heating at 400° to 1,000° C. thereby preparing a molecular sieving carbon adsorbent. This process is understood as a process of adsorbing the said synthetic resin material substance along with catalyst on prepared activated carbon having great pores and then again treating for its carbonization.

Japanese Patent Publication No. 47,758/1977 discloses a process of heating saran wastes at high temperatures, then pulverizing and granulating by addition of a sintering agent, such as coal tar pitch, and a granulating agent, such as Avicell, followed by once again heating at a temperature of 400° to 900° C. for their dry distillation. This process gains the advantage of being capable of preparing the molecular sieving carbon using inexpensive raw materials (saran wastes).

Japanese Patent Publication No. 18,675/1977 discloses a process of treating a coke containing up to 5% of volatile components at a temperature of 600 to 900° C. for a time of 1 to 60 minutes or more by addition of hydrocarbons releasing carbons by their thermal decomposition thereby depositing the released carbons in pores of the coke and thus, preparing a carbon-containing molecular sieve used for the separation of gases having as small a molecular diameter as about 4Å or less.

Japanese Patent Publication No. 8,200/1979 discloses an apparatus designed for the production of oxygen-rich air by contacting air with a molecular sieving coke for selective adsorption of oxygen from the air and desorbing it under reduced pressure.

Japanese Laid-Open Patent Application No. 106,982/1974 discloses a process of impregnating coke with an organic compound having boiling points of 200° to 360° C. at normal pressure or reduced pressure thereby reducing overly great pores of the coke to 2 to 6Å and thus, preparing a molecular sieving coke suitable for the separation of $O_2$ and $N_2$, in particular.

Japanese Patent Publication No. 17,595/1979 discloses a process for the production of nitrogen-rich gases from gases containing at least oxygen in addition to nitrogen, such as air, using the molecular sieving coke prepared by the process disclosed in the said Japanese Patent Publication No. 18,675/1977.

Japanese Patent Publication No. 54,083/1983 discloses a process of molding a finely-divided charcoal, not activated carbon, or coke using a coking agent and dry distilling the resultant molding whereby preparing a carbon-containing adsorptive medium, including steps of pulverizing the charcoal, not activated carbon, or coke to a particle size of 100 micrometers or less, mixing with 5 to 20% by weight of a natural and/or synthetic rubber and 1 to 15% by weight of a thermoplastic substance, fabricating this mixture into a molding and heating the molding at about 400° to 1,400° C. at an inert atmosphere.

Further, Japanese Laid-Open Patent Application No. 45,914/1984 discloses a process of granulating a coconut shell powder using, as a binder, coal tar pitch and/or coal tar, dry distilling at 750° to 900° C., washing the dry-distilled carbon with an aqueous rare mineral acid solution, washing with water and drying and impregnating this dried one with 1–3% coal tar pitch and/or coal tar at 200° to 400° C., then enhancing the temperature up to 950° to 1,000° C., heat treating at this enhanced temperature for 10 to 60 minutes and taking out a product after cooling in an inert gas thereby preparing a molecular sieving carbon.

The object of the present invention is to provide a molecular sieving carbon having an extremely specific porous structure.

Another object of the present invention is to provide a molecular sieving carbon which is great in adsorption selectivity coefficient and diffusivity ratio rate and extremely great in adsorption capacity.

Still another object of the present invention is to provide a process for the production of the said molecular sieving carbon of the present invention.

Another further object of the present invention is to provide use of the said molecular sieving carbon of the present invention for the separation of certain gas mixtures on the basis of the finding that the said molecular sieving carbon is optimum for the separation of such gas mixture.

Other further objects and advantages of the present invention will be clear from following explanations.

According to the present invention, the said objects and advantages of the present invention can be achieved by a molecular sieving carbon characterized by (A) having a structure in which a number of spherical carbonaceous particles having a particle diameter of 0.8 to 120 micrometers overlap and coalesce three-dimensionally at random, (B) in which continuous pathways running three-dimensionally at random exist between a number of the carbonaceous particles, (C) in which a number of the carbonaceous particles have each a number of pores communicating with the pathways existing between the particles, and (D) having a carbon content of at least 85% by weight.

FIGS. 1 and 2 of the accompanying drawings are scanning electron microscopic photographs of the molecular sieving carbon of the present invention (magnification: about 300× in FIG. 1 and about 1,000× in FIG. 2).

Figure 1:
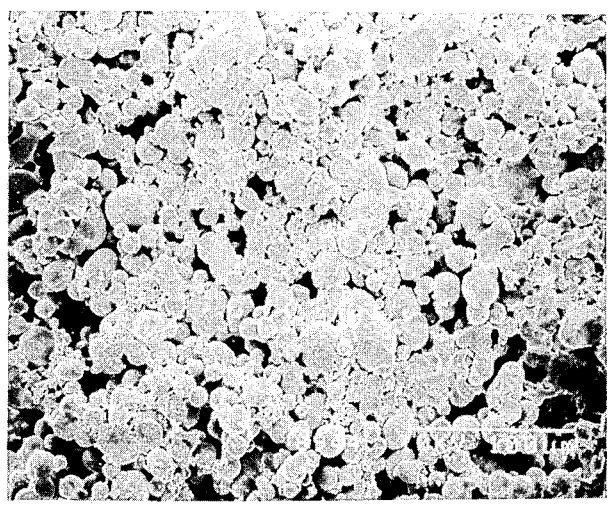

Further, according to the present invention, the said molecular sieving carbon of the present invention is prepared by a process for the production of a molecular sieving carbon which comprises (1) preparing an intimate mixture comprising
 (A) a finely-divided thermosetting phenol resin, said finely-divided thermosetting phenol resin being specified as
  (a) comprising primary spherical particles of a phenol resin having a particle diameter of 1 to 150 micrometers or the said primary spherical particles and their secondary coagulated substance,
  (b) of which at least 50% by weight of the whole having a size capable of passing through a 100 Tyler mesh sieve,
  (c) satisfying the following formula:

$$D_{900-1015}/D_{1600}=0.2-9.0$$

$$D_{890}/D_{1600}=0.09-1.0$$

in the case where in the infrared absorption spectrum by KBr tablet method, the absorption intensity of a peak at 1600 cm$^{-1}$ is expressed as $D_{1600}$, the absorption intensity of the greatest peak in the range of 900–1015 cm$^{-1}$ as $D_{900-1015}$, and the absorption intensity of a peak at 890 cm$^{-1}$ as $D_{890}$, and,
  (d) having a solubility in methanol under reflux of 50% by weight or less,
 (B) a solution of a thermosetting resin of which the thermosetting resin being a phenol resin or melamine resin, and
 (C) a high polymer binder, said high polymer binder being selected from polyvinyl alcohols and water-soluble or water-swellable cellulose derivatives,
said intimate mixture containing 5 to 50 parts by weight (as solids) of the solution of the thermosetting resin (B) and 1 to 30 parts by weight of the high polymer binder (C) per 100 parts by weight of the finely-divided thermosetting phenol resin (A), (2) molding the said intimate mixture into a particulate substance, and (3) heat treating the particulate substance at a temperature falling in the range of 500° to 1,100° C. under a non-oxidizing atmosphere whereby forming a carbonized particulate product.

The finely-divided thermosetting phenol resin (A) used in the step (1) in the process of the present invention is composed of primary spherical particles of a phenol resin having a particle diameter of 1 to 150 micrometers or the said primary spherical particles and their secondary coagulated substance. The primary spherical particles should preferably have a particle diameter falling in the range of 2 to 80 micrometers.

Further, at least 50% by weight of the said fine powder (A) as a whole has a size capable of passing through a 100 Tyler mesh sieve. More preferably, at least 90% by weight of the fine powder (A) has a size capable of passing through a 100 Tyler mesh sieve. The fine powder (A) contains methylol groups in adequate but considerable proportions. That is, the fine powder (A) satisfies the following formula:

$$D_{900-1015}/D_{1600}=0.2-9.0, \text{ and}$$

$$D_{890}/D_{1600}=0.09-1.0$$

in the case where in the infrared absorption spectrum by KBr tablet method, the absorption intensity at 1600 cm$^{-1}$ (absorption peak ascribable to the benzene) is expressed as $D_{1600}$, the greatest absorption intensity in the range of 900–1015 cm$^{-1}$ (absorption peak ascribable to the methylol group) as $D_{900-1015}$, and the absorption intensity at 890 cm$^{-1}$ (absorption peak of the isolated hydrogen atom in the benzene nucleus) as $D_{890}$.

The value of a ratio of $D_{900-1015}/D_{1600}$ falls preferably in the range of 0.3 to 7.0 and more preferably in the range of 0.4 to 5.0.

Moreover, the fine powder (A) is also specified as having a solubility in methanol under reflux of 50% by weight or less.

The methanol solubility referred to here is determined by the following formula by precisely weighing about 100 g of a sample (the precisely-weighed weight is called C), heat-treating in about 500 ml of 100% methanol under reflux for 30 minutes, then filtering through a glass filter, further washing the filter residue sample with about 100 ml of methanol on the filter and then drying the filter residue sample at a temperature of 100° C. for 2 hours (the precisely-weighed weight is called D).

$$\text{Methanol solubility (\%)} = \frac{C - D}{C} \times 100$$

The methanol solubility defined by the above formula is the property of the said finely-divided phenol resin (A) that exhibits itself by its having a structure that it is properly controlled for its crosslink density and contains a considerably great amount of methylol groups.

That is, when the crosslink density is lower and the content of methylol groups is greater, the methanol solubility is greater and on the contrary, when the crosslink density is higher and the content of reactive methylol groups is reduced, the methanol solubility goes lower. The methanol solubility of the finely-divided phenol resin (A) used in this invention is preferably 1 to 40%, and more preferably 2 to 35%.

The finely-divided phenol resin (A) used in the present invention can be prepared by contacting phenols with a hydrochloric acid-formaldehyde bath containing hydrochloric acid (HCl) in a concentration of 5 to 28% and formaldehyde (HCHO) in a concentration of 3 to 25% maintaining the bath so as to reach 8 or more in a bath ratio represented by the following formula (I)

$$\text{Bath ratio} = \frac{\text{Weight of said hydrochloric acid-formaldehyde bath}}{\text{Weight of phenols}} \quad \text{(I)}$$

said contact being effected in such a manner that a white turbidity is formed after phenols are contacted with the bath and then at least spherical pink solids are formed.

As the phenols phenol is most favorable, but provided that at least 70% by weight (called "%" for short hereinafter), and particularly at least 75%, of phenols is contained, they may be mixtures with one or more of known phenol derivatives, such as o-cresol, m-cresol, p-cresol, bis-phenol A, o-, m- or p-$C_2$-$C_4$ alkylphenol, p-phenylphenol, xylenol, hydroquinone or resorcin and the like. The feature of the above manufacture method lies in contacting an aqueous hydrochloric acid-formaldehyde solution obtained by setting hydrochloric acid concentrations in considerably high concentrations and containing an excess of formaldehyde with respect to phenol with phenol at a bath ratio of 8 or more and preferably at as great a ratio as 10 or more. Such phenol-formaldehyde reaction conditions differ basically from known novolak resin and resol resin reaction conditions. That is, as compared with conventional novolak resin production, they are the same in the respect of using acid catalyst, but they differ in the respect that in this manufacture method, the concentration of the acid catalyst is considerably higher and the formaldehyde concentration as well is considerably higher as compared with the novolak resin production. That is, the novolak resin is usually prepared by reacting phenol and formalin in the presence of such an acid catalyst as oxalic acid (usually 0.2 to 2%) in condition of such an excess of phenol as to reach 1/0.7 to 1/0.9, for instance, in a molar ratio (A)/(B) of phenol (A) and formaldehyde (B). The novolak resin obtained by such a method is based on tri- to pentamers containing phenol nuclei linked by methylene groups, and contains hardly any activity-rich methylol groups. Consequently, the novolak resin per se is not self-crosslinkable and is thermoplastic. Such novolak resins become setting resins by reacting under heat with a crosslinking agent being a formaldehyde-generating agent in itself while at the same time as being an organic base (catalyst)-generating agent, such as hexamethylenetetramine (hexamine), or by heat reacting after mixing, for instance, with a solid acid catalyst and paraformaldehyde and the like. Consequently, with the difference in the manufacture method the finely-divided phenol resin (A) used in the present invention differs completely from novolak resins.

Further, as compared with conventional production of resol resins, they are the same in the respect of using of an excess of formaldehyde, but unlike the production of resol resins, acid catalysts are used.

Resol resins are prepared by causing the reaction by setting a molar ratio (A)/(B) of phenol (A) to formaldehyde (B) at conditions of such an excess of formaldehyde as to be 1½ in the presence of a basic catalyst (about 0.2 to 2%), such as sodium hydroxide, ammonium and organic amine. Resol resins so obtained are based on mono- to trimers of phenols containing relatively great amounts of activated methylol groups, and because of their extremely great reactivity they are usually used as 60% or less, as solids, of an aqueous or methanol solution. These resol resins, because of extremely high reactivity, cannot be solids being stabilized over a prolonged period of time as a granule or powder, and their cured substances, because of a high degree of progress of their three-dimensional structure, are greater in hardness, and it is very difficult to turn them into a fine powder.

Consequently, the finely-divided phenol resin (A) used in the present invention differs altogether from resol resins.

The said manufacture method of the fine powder (A) used in the present invention is disclosed, for instance, in Japanese Laid-Open Patent Application No. 177,011/1982 and 111,822/1983.

The fine powder (A) used in the present invention generally has the characteristics that a weight increase ratio in acetylation is 23 to 80%. The weight increase ratio in acetylation referred to here is determined by the following formula by precisely weighing about 10 g of a dried sample (the precisely-weighed weight is called A), adding this precisely-weighed sample in about 300 g of an acetylation bath comprising 78% acetic anhydride, 20% acetic acid and 2% o-phosphoric acid, then heating by enhancing the temperature from room temperature up to 115° C. in 45 minutes, further holding at 115° C. for 15 minutes, then quenching, suction filtering on a glass filter, thoroughly washing with deionized water on the filter, then washing with a small amount of cold methanol, drying the filter residue at 70° C. for 2 hours and further leaving in a desiccator for 24 hours (the dried weight of the filter residue is called B).

$$\text{Weight increase ratio in acetylation (\%)} = \frac{B - A}{A} \times 100$$

The said characteristics that the said weight increase ratio in acetylation is 23 to 80% indicate the fact that the phenol resin powder contains methylol groups and acetylable phenolic hydroxyl groups corresponding to the said weight increase ratio in acetylation.

The solution of the thermosetting resin (B) being another raw material used in the step (1) in the process of the present invention is a solution of a phenol resin or melamine resin.

As the solution of the phenol resin there are cited, for instance, liquid resol resins or novolak resins. Resol resins are initial products obtained by reacting phenols and aldehydes in the presence of basic catalysts, and usually they are self-heat-crosslinkable phenol resins with molecular weight about 600 or less being enriched with methylol groups. Usually, they are often used as liquid resins in methanol or acetone as solvent, but they are also used as water-soluble resol resin maintaining in stabilized water-soluble condition initial condensates obtained by reacting 1.5 to 3.5 moles of aldehydes for 1 mole of phenol in the presence of a somewhat excess of an alkali catalyst. As curing catalysts to accelerate the curing of resol resins there may be used inorganic acids, such as sulfuric acid, hydrochloric acid and the like, and organic acids, such as oxalic acid, acetic acid, paratoluenesulfonic acid, maleic acid, malonic acid and the like. Novolak resins, as mentioned above, are obtained by reacting phenol and formalin in the presence of an acid catalyst, such as oxalic acid, formic acid, hydrochloric acid and the like, in condition of such an excess of phenol as to reach 1/0.7 to 1/0.9, for instance, in a molar ratio of phenols and aldehydes. They may be fed as liquid resins in methanol, acetone and the like as solvent. These novolak resins can be cured by reacting under heat by addition of hexamethylenetetramine (hexamine).

Melamine resins are initial melamine-formaldehyde condensates and because of being water-soluble they can be used as aqueous solutions. As curing agents for melamine resins there can be used inorganic acids, such as hydrochloric acid, sulfuric acid and the like, carboxylate esters such as dimethyl oxalate esters, and hydrochlorides of amines such as ethylamine hydrochloride and triethanolamine hydrochloride.

Furthermore, the high polymer binder used in the said step (1) is polyvinyl alcohols or water-soluble or water-swellable cellulose derivatives. As polyvinyl alcohols there are favorably used those which have a polymerization degree of 100 to 5,000 and saponification degree of 70% or more. There are also favorably used those which are in part modified with carboxyl groups.

Further, as cellulose derivatives there are favorably used, for instance, methyl cellulose, carboxymethyl cellulose, hydroxypropylmethyl cellulose and the like. Cellulose derivatives can be used as having various viscosities according to the amount of methoxy groups ($-OCH_3$) or hydroxypropoxy groups ($-OC_3H_6OH$) introduced, polymerization degree and the like.

The step (1) in the process of the present invention is carried out by mixing the said finely-divided thermosetting phenol resin (A), solution of the thermosetting resin (B) and high polymer binder (C).

On that occasion, 5 to 50 parts by weight, as solids, of the solution of the thermosetting resin (B) and 1 to 30 parts by weight of the high polymer binder (C) are used for each 100 parts by weight of the finely-divided thermosetting phenol resin (A). Further, preferably 7 to 40 parts by weight, and more preferably 10 to 30 parts by weight, of the solution of the thermosetting resin (B), and preferably 2 to 20 parts by weight, and more preferably 3 to 15 parts by weight, of the high polymer binder are used per 100 parts by weight of the finely-divided thermosetting phenol resin (A).

For the mixture of the components (A), (B) and (C) the said components (A), (B) and (C) may be mixed as such, or they may also be intimately mixed in the presence of water by adding water, for instance, beside the components (A), (B) and (C). Water may also be added, for instance, as component (C) dissolved in water before the components (A), (B) and (C) are mixed. Water is used preferably in amounts of 5 to 30% by weight, and more preferably 8 to 20% by weight, based on the intimate mixture (as solids) obtained in the step (1).

In the case, further, of carrying out the step (1) in the process of the present invention, in addition to the components (A), (B) and (C), there may be used, for instance, starch, its derivative or modified substance in amounts of 5 to 50 parts by weight, and more preferably 10 to 40 parts by weight, per 100 parts by weight of the finely-divided thermosetting phenol resin (A).

As the said compounds, such as starch, there may be used starch such as potato starch and corn starch; starch derivatives, for instance, esterified starch such as starch acetate, starch sulfate and starch phosphate; etherified starch such as hydroxyalkyl starch and carboxymethyl starch; crosslinked starch such as distarch phosphate and glycerol distarch, or modified starch such as enzyme-modified dextrin, and the like. These components, such as starch and the like, function favorably as pore-forming materials, and are believed to participate in the formation of pores due to the herein-below-described thermal decomposition at the time of carbonization in a non-oxidizing atmosphere. These components may be used, in the step (1), in condition where they were powder, or dispersed in water as powder, or in condition where they were heat treated with hot water, such as alpha-conversion treatment or the like.

Further, in the production of the molecular sieving carbon of the present invention, for instance, surface active agents such as ethylene glycol, polyoxyethylene fatty acid ester, polyoxyethylene alkyl ether, ammonium polycarbonate and so on, curing agents for liquid thermosetting resins, crosslinking agents for polyvinyl alcohols, plasticizers for extrusion granulation, finely-divided crystalline cellulose, finely-divided coconut shell, finely-divided coal, tar, pitch or other synthetic resins may be added in small amounts for the improvement of workability in the range not to lose its characteristics.

For the preparation of the intimate mixture in the step (1) the said raw materials can be mixed, for instance, in a ribbon mixer, V type mixer, cone mixer, kneader and the like.

For instance, the step (1) can be carried out by dry mixing a predetermined amount of the finely-divided thermosetting phenol resin (A) optionally by addition of starch and the like in these mixers and then thoroughly mixing by addition of a predetermined amount of the solution of the thermosetting resin (B) and the high polymer binder (C), such as polyvinyl alcohol, prepared beforehand by dissolving in hot water.

According to the process of the present invention the intimate mixture prepared in the step (1) is then molded into a particulate substance in the step (2). The molding of the particulate substance is effected, for instance, by means of mono- or bi-axial wet extrusion granulator, vertical type granulator, such as basket RYUZER (pelletizer), semi-dry type disk pelletizer and the like.

The granulate substance granulated by means of wet extrusion granulator, in particular, is favorable because of being greater in particle strength as well as of being greater in separability of the carbonized molecular sieving carbon. The form of the particulate substance is, for instance, columnar or spherical. The size of the particulate substance obtained by the granulation in the step (2) is not particularly restricted, but in the case, for instance, of its being columnar, it should preferably be of the order of 0.5 to 5 mm in diameter and 1 to 10 mm in length, whereas in the case of its being spherical, it should preferably be of the order of 0.5 to 10 mm in diameter.

The particulate substance formed in the step (2) is then heat treated at a temperature falling in the range of 500° to 1,100° C. under a non-oxidizing atmosphere in the step (3) whereby a carbonized particulate product is formed.

The non-oxidizing atmosphere may be, for instance, $N_2$, Ar or He.

In the case where the heat treatment temperature in the step (3) is lower than 500° C., there is a great tendency that all that are obtained are carbonized products which are smaller in specific surface area, not sufficient in adsorption capacity and lower in adsorption selectivity, and in the case where the said temperature is higher than 1,100° C., carbonized products obtained cause the shrinkage of pores and after all, there is likewise a great tendency that all that are obtained are carbonized products which are reduced in specific surface area and micropore volume with lower adsorption capacity.

The preferred heat treatment temperature in the step (3) is 600° to 1,000° C., and the more preferred heat treatment temperature is 650° to 950° C.

Furthermore, until the heat treatment in the step (3) is reached, temperature-enhancing rate is preferably 5° to 300° C./hr and more preferably 10° to 180° C./hr and most preferably 15° to 120° C./hr.

According to the present invention, successively to the step (3), the carbonized particulate product can be heat treated at a temperature falling in the range of 500° to 1,000° C. under an oxidizing atmosphere until the carbonized particulate product is reduced in weight in the range up to 15% by weight.

The oxidizing atmosphere may be, for instance, air, $H_2O$, $CO_2$ or the like.

The heating temperature in the oxidizing atmosphere is preferably 600° to 1,000° C. and more preferably 650° to 950° C.

Thus, according to the present invention, as mentioned above, there is provided a molecular sieving carbon characterized by (A) having a structure in which a number of spherical carbonaceous particles having a particle diameter of 0.8 to 120 micrometers overlap and coalesce three-dimensionally at random, (B) in which continuous pathways running three-dimensionally at random exist between a number of the carbonaceous particles, (C) in which a number of the carbonaceous particles have each a number of micropores communicating with the pathways existing between the particles, and (D) having a carbon content of at least 85% by weight.

Figure 2:
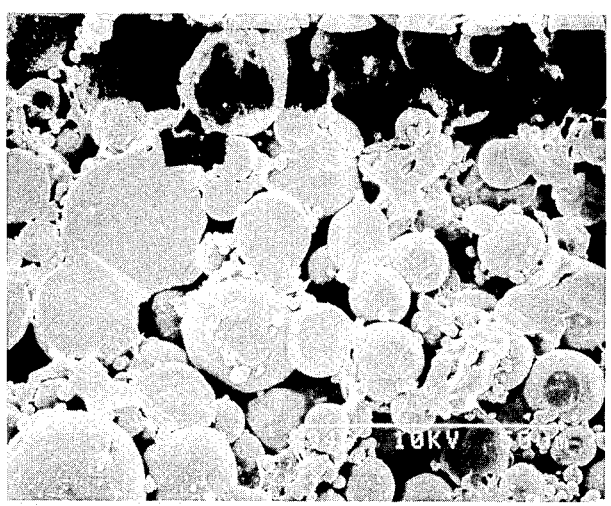

The structural features of (A) and (B) above with the molecular sieving carbon of the present invention are well expressed in scanning electron microscopic photographs of the accompanying FIGS. 1 and 2.

In the molecular sieving carbon of the present invention a number of spherical carbonaceous particles have a particle diameter of 2 to 80 micrometers.

Further, for the characteristic of (B) above, in the molecular sieving carbon of the present invention, continuous pathways existing between a number of carbonaceous particles should preferably have an average diameter of 0.1 to 20 micrometers.

In the molecular sieving carbon of the present invention, coupled with the said features (A) and (B), a number of the carbonaceous particles have each a number of micropores communicating with the pathways existing between the said particles. The existence of a number of these micropores contribute greatly to the exhibition of selective adsorbability of the molecular sieving carbon of the present invention.

The micropores in a number of the carbonaceous particles should preferably have an average diameter of about 10Å or less.

Moreover, the volume accounted for by the micropores is preferably 0.1 to 0.7 cc, more preferably 0.15 to 0.5 cc, and most preferably 0.2 to 0.4 cc, per gram of weight of the molecular sieving carbon.

The molecular sieving carbon of the present invention, as the feature in composition, has the carbon content of at least 85% by weight, and preferably at least 90% by weight.

As is understood from the said manufacture process, in the molecular sieving carbon of the present invention a number of the said spherical carbonaceous particles are believed to be derived from spherical particles of a phenol resin having a particle diameter of 1 to 150 micrometers.

The molecular sieving carbon of the present invention should preferably have a porosity of 25 to 50% by volume, and more preferably 30 to 45% by volume.

The molecular sieving carbon of the present invention should preferably have a bulk density of 0.7 to 1.2 g/cc, and more preferably 0.8 to 1.1 g/cc.

The molecular sieving carbon of the present invention, as mentioned above, should preferably have micropores with an average diameter of 10Å or less, and these micropores should preferably be most greatly distributed in the range of average diameter 3 to 5Å. Further, it can also be said to be characteristic of the molecular sieving carbon of the present invention that it contains pores greater than this, such as pores with an average diameter of 15 to 200Å, in as small a pore volume as to be usually 0.2 cc/g or less, preferably 0.15 cc/g or less, and more preferably 0.1 cc/g or less.

The molecular sieving carbon of the present invention has a specific surface area, as values measured by the B.E.T. method by $N_2$ adsorption, of the order of usually 5 to 600 $m^2/g$, preferably 10 to 400 $m^2/g$, and most preferably 20 to 350 $m^2/g$.

In this regard, usually-used activated carbon having a specific surface area of 1,000 to 1,500 $m^2/g$ has the maximum value of the pore size distribution of micropores in the range of the order of 15Å or more in pore diameter, and the volume of pores having a pore diameter falling in the range of 15 to 200Å is of the order of 0.4 to 1.5 cc/g, and it does not have such molecular sieve characteristics as with the molecular sieving carbon of the present invention.

The molecular sieving carbon of the present invention is usually provided, for instance, in a columnar or spherical form. The molecular sieving carbon of the present invention is in a 0.5 to 5 mm across and 1 to 10 mm long columnar or 0.5 to 10 mm across spherical form.

The molecular sieving carbon of the present invention, as mentioned above, can very readily be prepared, and has superior adsorption capacity and selective adsorption characteristics. Because of this, the molecular sieving carbon of the present invention can be used for the separation of various mixed gases. It can be used for the separation of, for instance, a gaseous mixture of nitrogen gas and oxygen gas, gaseous mixture of methane gas and hydrogen gas, mixture of hydrocarbon isomers, such as xylene isomer, butane isomer, butene isomer and the like, mixture of ethylene and propylene, gaseous mixture of hydrogen and carbon monoxide, gaseous mixture containing argon, and the like. More specifically, it can be used, for instance, for obtaining a nitrogen gas, oxygen gas or gaseous mixture enriched with either the nitrogen gas or the oxygen gas from a gaseous mixture containing the nitrogen gas and oxygen gas, or for obtaining a methane gas, hydrogen gas or gaseous mixture enriched with either the methane gas or hydrogen gas from a gaseous mixture containing the methane gas and hydrogen gas.

Because of this, it is desirable to employ the pressure swing adsorption method. By this method, other than the above, there can be carried out the recovery of hydrogen from steam reforming gas, ethylene plant offgas, methanol decomposition gas, ammonia decomposition gas, coke furnace exhaust gas and the like, or the recovery of carbon monoxide from converter exhaust gas, and the like, which can produce favorable results.

In the next place, the measurement methods used in the present invention will be indicated hereinunder,
(1) Measurement of the pore volume and pore size distribution The pore volume and the pore size distribution of the molecular sieving carbon of the invention are measured by a mercury penetration method using a porosimeter (Poresizer 9310 made by Shimazu Seisakusho) for pores with a diameter ranging of from 60Å to 500 micrometers.

For pores with a diameter of less than 60Å, they are determined by the following Kelvin equation from the adsorption isotherm of nitrogen gas.

$$\ln P/P_o = \frac{-2 V\gamma\cos\theta}{r_k RT}$$

P: saturated vapor pressure of the gas when it is adsorbed to pores
$P_o$: saturated vapor pressure of the gas in a normal condition
$\gamma$: surface tension
V: volume of one molecule of liquid nitrogen
R: gas constant
T: absolute temperature
$r_k$: the Kelvin radius of the pores Correction for the Kelvin radius of pores was made by the Cranston-Inkley method.

(2) Gas concentration analysis

Analyzed using Shimazu gas-chromatograph GC-9A and oxygen concentration analyzer (Model 0260) made by Beckman Co.

The present invention will be explained in more detail with the reference to Examples hereinunder. In Tables, marks indicated in overall evaluations are ranked in the following order:

Good ⓞ>○>X not good.

EXAMPLE 1

Charged into a 400 liter reaction vessel was 300 kg of a mixed aqueous solution of 18% hydrochloric acid and 9% formaldehyde, and the temperature was set at 20° C. Then, in this reaction vessel 12 kg of 90% concentration of an aqueous phenol solution (20° C.) prepared by the use of 98% concentration (2% water) of phenol and water was added. After its addition the mixture was stirred for 30 to 40 seconds, and the contents of the reaction vessel turned turbid rapidly, stirring was simultaneously stopped and it was left alone. On continued standing the inner temperature was slowly enhanced, the contents discolored slowly to a light pink and 30 minutes after it went turbid, a slurry-like or resinous product was observed to form. The above reaction was repeated for 6 batches, and for the remaining 5 batches, excepting for the first batch (Referential Example), of them, following on the said step, the temperature of the contents was successively enhanced up to 75° to 65° C. in 30 minutes, and with stirring at this temperature the contents were held for a given period of time as indicated in Table 1. Then, the contents were washed with water, then neutralized for 6 hours at 50° C. in 0.1% concentration of an aqueous ammonia solution, then washed with water, filtered and dried at 80° C. for 6 hours. As a result, there was obtained the intended phenol resin powder being spherical in particle form. Solubility in methanol under reflux (called methanol solubility hereinafter) of this phenol resin powder was measured according to the said test method.

Then 10 kg of the spherical phenol resin powder of each batch prepared by the said procedure was weighed, and further, with regard to 100 parts by weight of this spherical phenol resin powder 16 parts by weight, as solids, of a water-soluble resol resin (SHONOL, BRL-2854, a product of Showa Highpolymer Co., Ltd., solids concentration 60% by weight), 2.7 parts by weight of polyvinyl alcohol with a polymerization degree of 1,700 and saponification degree of 88%, 1.3 parts by weight of polyvinyl alcohol with a polymerization degree of 500 and saponification degree of 99% and 13 parts by weight of potato starch were weighed.

Of the said raw materials, first, the spherical phenol resin powder and potato starch were dry mixed for 15 minutes in a kneader. On the other hand, the said polyvinyl alcohol was dissolved with hot water so as to become 15% by weight of an aqueous solution, and this polyvinyl alcohol solution and the water-soluble resol resin were added in a kneader and further mixed for 15 minutes.

This mixed composition was extruded by a biaxial extrusion-granulator (Pelleter-Double, EXDF-Model 100, made by Fuji Paudal K. K.) and granulated into granular substances 3 mm$\phi$ in average particle size × 6 mmL. The granulated substances were heat treated at 80° C. for 24 hours, then 500 g each of the granular substances were taken and put in a rotary kiln 100$\phi$×1,000 mmL in effective size, the temperature was enhanced at 60° C./hr under a nitrogen atmosphere and they were held at 750° C. for 1 hour and then the kiln was cooled whereby particulate carbonized products were obtained.

Figure 3:
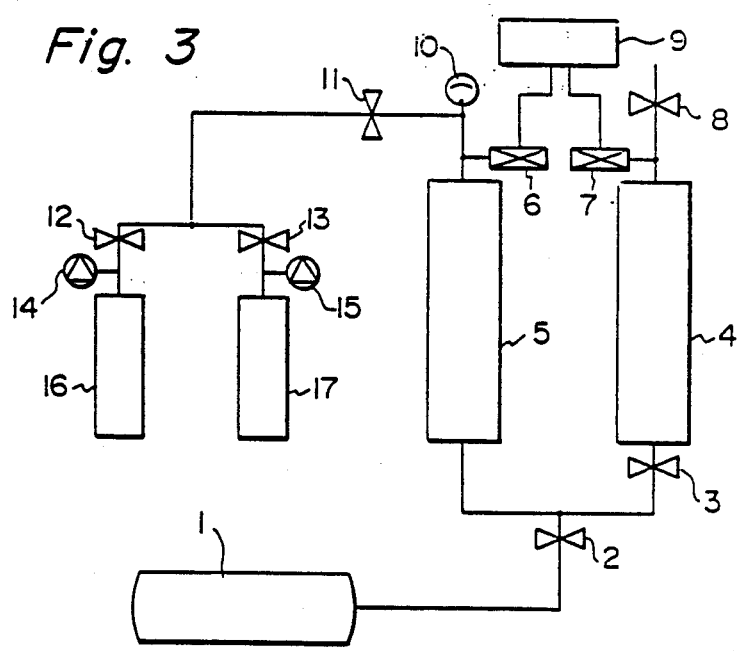
FIG. 3 is a flow chart for the apparatus used for the measurement of adsorption characteristics of the molecular sieving carbon of the present invention.

In order to evaluate the molecular sieving characteristics of this particulate carbonized product amounts of nitrogen gas and oxygen gas adsorbed were measured by means of adsorption characteristic measuring apparatus shown in FIG. 3. In FIG. 3 about 13 g of a sample was charged into a sample chamber 4 (226.9 ml), valves 11, 8 were closed, valves 2, 3 were opened to deaerate for 30 minutes, then the valves 2, 3 were closed, the valve 11 was opened to forward oxygen gas or nitrogen gas into a control chamber 5 (231.7 ml), when a set pressure (6.88 kg/cm$^2$) was reached, the valve 11 was closed, the valve 3 was opened to measure the change of the inner pressure in a predetermined period of time whereby adsorption rate of each of oxygen and nitrogen was determined. Nitrogen and oxygen separation functions were determined by the amount of nitrogen adsorbed ($Q_1$) and amount of oxygen adsorbed ($Q_2$) 1 minute after adsorption was initiated and the difference in adsorbed amount ($\Delta Q$) represented by the following equation (II)

$$\Delta Q = Q_2 - Q_1 \qquad (II)$$

and the selectivity coefficient of the following equation (III)

$$\alpha = \frac{Q_2/P_2}{Q_1/P_2} \qquad (III)$$

in which $P_1$ is a nitrogen adsorption pressure and $P_2$ is an oxygen adsorption pressure.

The results of the above Example 1 were indicated in Table 1.

In this connection, in FIG. 3, 1 ... vacuum pump, 2, 3, 8, 11, 12 and 13 ... valve, 4 ... sample chamber, 5 ... control chamber, 6 and 7 ... pressure sensor, 9 ... recorder, 10 ... pressure gauge, 14 and 15 gas regulator, 16 ... nitrogen cylinder and 17 ... oxygen cylinder.

TABLE 1

|  |  | Example 1 |  |  |  |  | Referential Example |
|---|---|---|---|---|---|---|---|
|  |  | Sample 1 | Sample 2 | Sample 3 | Sample 4 | Sample 5 |  |
| Phenol resin powder | Holding time at 75° C. (minute) | 10 | 20 | 30 | 40 | 60 | 0 |
|  | IR intensity $D_1$ | 1.21 | 1.22 | 1.11 | 0.91 | 0.83 | 1.22 |
|  | $D_2$ | 0.12 | 0.13 | 0.11 | 0.09 | 0.08 | 0.19 |
|  | Methanol solubility (%) | 32 | 16 | 5 | 2.4 | 0.5 | 75 |
|  | Average particle diameter (μm) | 28 | 27 | 29 | 28 | 29 | 26 |
| Particulate carbonized product | $O_2$ adsorption Adsorption pressure (kg/cm$^2$) | 3.191 | 3.170 | 3.020 | 2.956 | 3.125 | 3.291 |
|  | Adsorbed amount (mg/g) | 16.3 | 18.6 | 23.7 | 26.0 | 19.1 | 12.3 |
|  | $N_2$ adsorption Adsorption pressure (kg/cm$^2$) | 3.471 | 3.413 | 3.410 | 3.556 | 3.500 | 3.321 |
|  | Adsorbed amount (mg/g) | 4.1 | 5.9 | 6.4 | 3.1 | 2.7 | 9.6 |
|  | Difference in adsorbed amount ΔQ (mg/g) | 12.2 | 12.7 | 17.3 | 22.9 | 16.4 | 2.7 |
|  | Selectivity coefficient α | 4.3 | 3.4 | 4.2 | 10.1 | 7.9 | 1.3 |
| Overall evaluation |  | ○ | ○ | ○ | ⊙ | ○ | X |

Note:
IR intensity ratios $D_1$ and $D_2$ were calculated by the following equations.
$D_1 = D_{900-1015}/D_{1600}$, $D_2 = D_{890}/D_{1600}$ As indicated in Table 1, in the case of using, as raw material, the spherical phenol resin powder having a methanol solubility of 50% or less, particulate molecular sieving carbons having good separability could be obtained.

Further, Referential Example uses, as the spherical phenol resin powder being raw material, one which is in excess of 50% by weight in methanol solubility with a lower crosslink degree, and the molecular sieving carbon obtained is considerably inferior in functions.

Example 2

A predetermined amount of polyvinyl alcohol having a polymerization degree of 1,000 and saponification degree of 88% was dissolved with hot water to make 20% by weight of an aqueous solution.

Separately from this, a spherical phenol resin powder having a methanol solubility of 2.4% with an average particle diameter of 28 micrometers prepared in like manner as the sample 4 in Example 1, water-soluble resol resin (SHONOL BRL-2854, a product of Showa Highpolymer Co., Ltd., solids concentration 60% by weight), water-soluble melamine resin (Sumitex Resin M-3, a product of Sumitomo Chemical Co., Ltd., solids concentration 80% by weight), methyl cellulose powder (METHOLOSE, 60SH-4000, a product of Shin-etsu Chemical Industry Co., Ltd.), potato starch and ethylene glycol were weighed for their respective predetermined amounts.

The said spherical phenol resin powder, potato starch and methyl cellulose powder were dry mixed for 15 minutes in the kneader, then aqueous polyvinyl alcohol solution, water-soluble resol resin, water-soluble melamine resin and ethylene glycol were added and further mixed for 15 minutes. This mixed composition was extruded by means of biaxial extrusion granulator (Pelleter-Double Model EXDF-100 made by Fuji Paudal K. K.) and columnar pellets having 6 kinds of compositions indicated in Table 2 were prepared. These columnar pellets were 3φ in average particle size ×6 mmL. These pellets were hardened and dried at 80° C. for 24 hours, then 500 g of the pellets were put in the rotary kiln 100φ×1,000 mmL in effective size, the temperature was enhanced up to 900° C. at 10° C./hr under 2 liters/min. of a nitrogen stream, they were held at this temperature for 1 hour and then the kiln was cooled.

Nitrogen and oxygen separation functions of particulate carbonized products so obtained were measured in like manner as in Example 1. The results were indicated in Table 2.

TABLE 2

|  |  |  | Sample |  |  |  |  |  |
|---|---|---|---|---|---|---|---|---|
|  |  |  | 6 | 7 | 8 | 9 | 10 | 11 |
| A | Spherical phenol resin powder |  | 100 | 100 | 100 | 100 | 100 | 100 |
| B | Water-soluble resol resin (solids) |  | 48 | 2.9 | 11.8 | 8.8 | 5.9 | 1.1 |
|  | Melamine resin (solids) |  | 24 | 1.5 | 5.4 | 3.8 | 2.4 | 1.1 |
| C | Water-soluble high polymer binder | Polyvinyl alcohol | 6 | 10.3 | 2.9 | 3.0 | 2.4 | 1.1 |
|  |  | Methyl cellulose | 4 | 25 | 11.8 | 0 | — | 0 |
| D | Starch |  | 18 | 7.4 | 14.7 | 10 | 7.1 | 2.1 |
|  |  | Sub-total | 200 | 147.1 | 146.6 | 125.6 | 117.8 | 105.4 |
| E | Ethylene glycol |  | 2 | 1.5 | 1.5 | 1.3 | 1.2 | 1.1 |
| F | Water* |  | 80 | 43.5 | 20.8 | 18.8 | 17.7 | 15.8 |
|  | Water ratio F/A + B + C + D |  | 0.40 | 0.296 | 0.142 | 0.15 | 0.15 | 0.15 |
|  | Workability at the time of granulation |  | X | Δ Impossible to granulate | ○ | ⊙ | ○ | ○ |
| $O_2$ adsorption | Adsorption pressure (kg/cm$^2$) |  | — | 3.420 | 3.118 | 2.976 | 3.068 | 3.148 |
|  | Adsorbed amount (mg/g) |  | — | 6.8 | 19.4 | 25.5 | 21.6 | 17.7 |
| $N_2$ adsorption | Adsorption pressure (kg/cm$^2$) |  | — | 3.555 | 3.418 | 3.523 | 3.481 | 3.245 |
|  | Adsorbed amount (mg/g) |  | — | 1.0 | 5.8 | 2.2 | 3.7 | 12.4 |
| Difference in adsorbed amount ΔQ (mg/g) |  |  | — | 5.8 | 13.6 | 23.3 | 17.9 | 5.3 |
| Selectivity coefficient α |  |  | — | 7.1 | 3.7 | 13.7 | 6.6 | 1.5 |

TABLE 2-continued

|  | Sample | | | | | |
| --- | --- | --- | --- | --- | --- | --- |
|  | 6 | 7 | 8 | 9 | 10 | 11 |
| Overall evaluation | X | X | ◯ | ◉ | ◯ | X |

*The amount of water is a total amount of water in water-soluble resol resin and water-soluble melamine resin, polyvinyl alcohol dissolving water, plus water added separately for adjustment of viscosity in the case of samples 6, 10 and 11.

In Table 2, sample 6 was no good in workability at the time of granulation and its granulation was impossible. In sample 7 using the water-soluble high polymer binder in greater amounts than in the stipulated proportions of the present invention, it was found to be less in amount of $O_2$ adsorbed and not to be favorable as the molecular sieving carbon.

Samples 8, 9 and 10 were favorable in amounts of $N_2$ and $O_2$ adsorbed and their separation characteristics obtained and particularly sample 9 was excellent in characteristics.

Sample 11 obtained from the raw material composition falling outside the limits provided for in the process of the present invention was found to be unfavorable because of being smaller in difference in $N_2$ and $O_2$ adsorbed amount as well as in selectivity coefficient.

EXAMPLE 3

Columnar pellet precursors 3 mm$\phi$ in average particle size × 6 mmL granulated using the same composition and the same conditions as with sample 9 in Example 2 were put in the rotary kiln 100$\phi$ × 1,000 mmL, the temperature was enhanced up to a given temperature at a temperature enhancing rate of 15° C./hr while passing 3 liters/min, of nitrogen, they were held at this temperature for 30 minutes and then the kiln was cooled whereby carbonized products were obtained.

Nitrogen and oxygen separabilities of the carbonized products were indicated in Table 3.

TABLE 3

|  |  | Sample | | | | |
| --- | --- | --- | --- | --- | --- | --- |
|  |  | 12 | 13 | 14 | 15 | 16 |
| Carbonization temperature °C. | | 450 | 700 | 950 | 1050 | 1200 |
| $O_2$ adsorption | Adsorption pressure (kg/cm$^2$) | 3.533 | 3.170 | 3.013 | 3.211 | 3.415 |
|  | Absorbed amount (mg/g) | 7.9 | 18.6 | 23.8 | 15.6 | 7.1 |
| $N_2$ adsorption | Adsorption pressure (kg/cm$^2$) | 3.991 | 3.455 | 3.565 | 3.682 | 3.695 |
|  | Adsorbed amount (kg/g) | 6.9 | 4.5 | 3.4 | 0.58 | 0.16 |
| Difference in adsorbed amount $\Delta Q$ (mg/g) | | 1.0 | 14.1 | 20.4 | 15.02 | 6.94 |
| Selectivity coefficient $\alpha$ | | 1.3 | 4.5 | 8.3 | 30.8 | 48.0 |
| Overall evaluation | | X | ◯ | ◉ | ◯ | X |

Sample 12 obtained by using a lower heat treatment temperature at the time of carbonization than the stipulated temperature of the present invention was less in amount of oxygen adsorbed and smaller in difference in adsorbed amount $\Delta Q$ as well as in selectivity coefficient $\gamma$ and was not favorable as the molecular sieving carbon. Samples 13, 14 and 15 are greater in all of amount of oxygen adsorbed, difference in adsorbed amount $\Delta Q$ and selectivity coefficient and are found to be practical as the molecular sieving carbon and particularly sample 14 is found to be excellent in characteristics.

Sample 16 obtained by using a higher heat treatment temperature at the time of carbonization than the stipulated temperature of the present invention is greater in selectivity coefficient $\gamma$, but unfavorably smaller in amount of oxygen adsorbed and difference in adsorbed amount $\Delta Q$.

EXAMPLE 4

Using a particulate molecular sieving carbon prepared in like manner as with sample 14 in Example 3, experiment with the separation of nitrogen and oxygen in the air was carried out by the pressure swing adsorption method (PSA).

Figure 4:
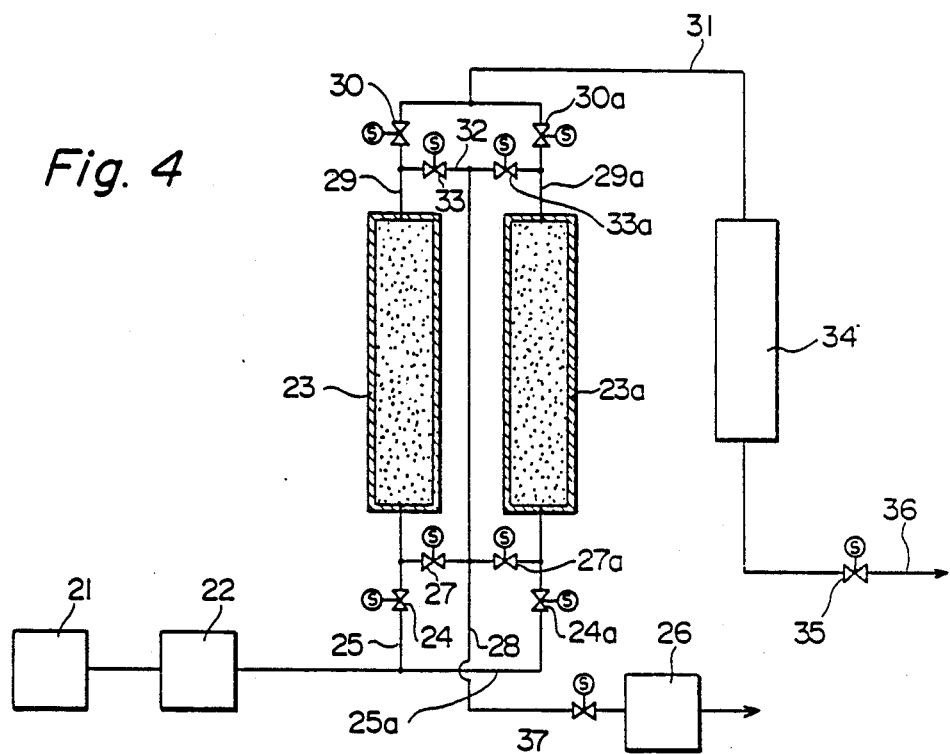
FIG. 4 is a flow chart for the pressure swing adsorption apparatus using the molecular sieving carbon of the present invention as adsorbent.

A schematic diagram of PSA apparatus used in the instant experiment was shown in FIG. 4. The size of the adsorption tower was 50$\phi$ in inner diameter × 1,000 mmL, and the said molecular sieving carbons (specific surface area 163 m$^2$/g) were packed in two adsorption towers. Their packing density was 0.58 g/cm$^3$.

First, air compressed by a compressor was forwarded to the adsorption towers, pressure at the time of adsorption was set at 4 kgf/cm$^2$-G in gauge pressure and desorption (evacuation) regeneration was effected by depressurizing down to about 100 torr by means of a vacuum pump. PSA operation was carried out in 5 steps of pressure equalization (elevation)—adsorption—pressure equalization (reduction)—evacuation—pressure elevation, and switchovers of the respective steps were effected by automated control over electromagnetic valves by a sequencer. PSA operation conditions were indicated in Table 4.

In the instant experiment purity of the product nitrogen gas was 99.9% ($N_2$+Ar) with its take-out amount of 1 l/min. and 99.7% with 2 l/min.

TABLE 4

|  | 30 seconds | 60 seconds | 10 seconds | 30 seconds | 60 seconds | 10 seconds |
| --- | --- | --- | --- | --- | --- | --- |
| Adsorption tower (1) | Pressure elevation (concurrent) | Adsorption (concurrent) | Pressure equalization (reduction) (concurrent) | Evacuation (countercurrent) | | Pressure equalization (elevation) (concurrent) |

TABLE 4-continued

| | 30 seconds | 60 seconds | 10 seconds | 30 seconds | 60 seconds | 10 seconds |
|---|---|---|---|---|---|---|
| Adsorption tower (2) | Evacuation (countercurrent) | | Pressure equalization (elevation) (concurrent) | Pressure elevation (concurrent) | Adsorption (concurrent) | Pressure equalization (reduction) (concurrent) |

In FIG. 4: 21 . . . air compressor, 22 . . . air drier, 23, 23a . . . adsorption tower, 24,24a . . . first switching valve, 25,25a . . . inflow path pipe, 26 . . . vacuum pump, 28 . . . suction path pipe, 29,29a . . . takeout path pipe, 31 . . . main pipe, 34 . . . reservoir tank, 36 . . . product gas take-out pipe, 27,27a,30,30a, 33,33a, 35,37 . . . switching valve.

EXAMPLE 5

Precursors having the same composition as used in Example 4 were carbonized for 1 hour at 850° C. in nitrogen atmosphere in like manner as in Example 4, and then successively activated for 10 minutes in a steam atmosphere. A sample taken out after cooling the kiln showed a reduction in weight of 5.2% by weight based on the weight of the carbonized product.

The particulate molecular sieving carbon obtained as the above was 620 m$^2$/g in specific surface area and 0.54 g/cm$^3$ in packing density.

The molecular sieving carbons were packed in the same PSA apparatus as used in Example 4 and there was conducted experiment to separate a material gas of 70% hydrogen gas and 30% methane by the PSA method.

The material gas kept in pressurized condition by means of compressor was admitted into adsorption towers and PSA operation was carried out by alternately repeating in the two towers 5 steps of pressure equalization (elevation)—pressure elevation—adsorption—pressure equalization (reduction)—evacuation. Adsorption pressure was set at 5 kgf/cm$^2$-G and regeneration was effected by depressurizing down to about 100 torr by means of vacuum pump. PSA operation conditions were indicated in Table 5.

In the instant experiment purity of the product hydrogen gas was 99.99% with its take-out amount of 2 l/min. and 99.91% with 4 l/min.

Hydrogen and methane, as mentioned above, could be separated in good condition by the particulate molecular sieving carbon obtained in the present invention.

TABLE 5

| | 30 seconds | 180 seconds | 10 seconds | 30 seconds | 180 seconds | 10 seconds |
|---|---|---|---|---|---|---|
| Adsorption tower (1) | Pressure elevation (concurrent) | Adsorption (concurrent) | Pressure equalization (reduction) (concurrent) | Evacuation (countercurrent) | | Pressure equalization (elevation) (concurrent) |
| Adsorption tower (2) | Evacuation (countercurrent) | | Pressure equalization (elevation) (concurrent) | Pressure elevation (concurrent) | Adsorption (concurrent) | Pressure equalization (reduction) (concurrent) |

What we claim is:

1. A molecular sieving carbon comprising a shaped object
   (A) which is an assembly of a number of contiguous, carbonaceous spheres having a diameter of 0.8 to 120 micrometers which spheres are bonded together three-dimensionally at random,
   (B) in which continuous interstitual pathways running three-dimensionally at random exist between a number of the carbonaceous spheres, said continuous pathways having an average diameter of 0.1 to 20 micrometers,
   (C) in which a number of the carbonaceous spheres each have a number of micropores communicating with the pathways existing between the spheres, said micropores having an average diameter of about 10Å or less and a volume of 0.1 to 0.7 cc/g,
   (D) having a carbon content of at least 85% by weight, and
   (E) having a bulk density of 0.7 to 1.2 gg/cc.

2. The molecular sieving carbon of claim 1 in which a number of the carbonaceous spheres have a diameter of 2 to 80 micrometers.

3. The molecular sieving carbon of claim 1 having a porosity of 25 to 50% by volume.

4. The molecular sieving carbon of claim 1 having a carbon content of at least 90% by weight.

5. The molecular sieving carbon of claim 1 in which a number of the carbonaceous spheres are derived from spheres of a phenol resin having a diameter of 1 to 150 micrometers.

6. The molecular sieving carbon of claim 1 in which the shaped object is a column having a width of 0.5 to 5 mm and a height of 1 to 10 mm long or a sphere having a diameter of 0.5 to 10 mm.

7. The molecular sieving of carbon of claim 1 in which said micropores have a volume of from 0.15 to 0.5 cc/g.

8. The molecular sieving carbon of claim 1 in which said micropores have a volume of from 0.2 to 0.4 cc/g.

9. The molecular sieving carbon of claim 1 having a porosity of from 30 to 45%.

10. The molecular sieving carbon of claim 9 in which said micropores have a volume of from 0.15 to 0.5 cc/g.

11. Porous carbon granules each consisting of a multitude of contiguous, carbonaceous spheres bonded in molded relationship, said spheres having a diameter of from 0.8 to 120 micrometers, said spheres having internal micropores having an average size of not more than 10 Angstrom units and most of said micropores having an average size of from 3 to 5 Angstrom units, the volume of said micropores being from 0.1 to 0.7 cc/g, said spheres having a volume of larger pores having an average size of from 15 to 200 Angstrom units of up to 0.2 cc/g, each of said granules having continuous, randomly disposed pathways between said spheres, said pathways having an average diameter of from 0.1 to 20 micrometers, said micropores communicating with said pathways, said granules being either columnar granules having a diameter of from 0.5 to 5 mm and a length of from 1 to 10 mm, or substantially spherical granules having a diameter of from 0.5 to 10 mm, said granules consisting of at least 85% by weight of carbon, and having a porosity of 25 to 50% by volume, a bulk density of 0.7 to 1.2 g/cc and a specific surface area, measured by the B.E.T. method of $N_2$ adsorption, of from 5 to 600 m²/g.

12. Porous carbon granules each consisting of a multitude of contiguous, carbonaceous spheres bonded in molded relationship, said spheres having a diameter of from 2 to 80 micrometers, said spheres having internal micropores having an average size of not more than 10 Angstrom units and most of said micropores having an average size of from 3 to 5 Angstrom units, the volume of said micropores being from 0.2 to 0.4 cc/g, said spheres having a volume of larger pores having an average size of from 15 to 200 Angstrom units of up to 0.1 cc/g, each of said granules having continuous, randomly disposed pathways between said spheres, said pathways having an average diameter of from 0.1 to 20 micrometers, said micropores communicating with said pathways, said granules being either columnar granules having a diameter of from 0.5 to 5 mm and a length of from 1 to 10 mm, or substantially spherical granules having a diameter of from 0.5 to 10 mm, said granules consisting of at least 85% by weight of carbon, and having a porosity of 30 to 45% by volume, a bulk density of 0.8 to 1.1 g/cc and a specific surface area, measured by the B.E.T. method of $N_2$ adsorption, of from 20 to 350 m²/g.

* * * * *

UNITED STATES PATENT AND TRADEMARK OFFICE
CERTIFICATE OF CORRECTION

PATENT NO. : 4 933 314
DATED : June 12, 1990
INVENTOR(S) : Chisato MARUMO et al

It is certified that error appears in the above-identified patent and that said Letters Patent is hereby corrected as shown below:

Column 18, line 17; change "gg/cc" to ---g/cc---.
           line 33; change "sieving of carbon" to
                    ---sieving carbon---.
           line 41; change "cc/g" to ---c/g---.
Column 19, line 11; delete the comma.

Signed and Sealed this

Twenty-eighth Day of April, 1992

Attest:

HARRY F. MANBECK, JR.

*Attesting Officer*            *Commissioner of Patents and Trademarks*